(12) United States Patent
Nelson et al.

(10) Patent No.: US 10,317,282 B2
(45) Date of Patent: Jun. 11, 2019

(54) SYSTEM AND METHOD FOR DETECTING TARGET MATERIALS USING A VIS-NIR DETECTOR

(71) Applicant: CHEMIMAGE CORPORATION, Pittsburgh, PA (US)

(72) Inventors: Matthew Nelson, Harrison City, PA (US); Patrick Treado, Pittsburgh, PA (US); Charles Gardner, Gibsonia, PA (US); Andrew Basta, Cranberry Township, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 15/401,716

(22) Filed: Jan. 9, 2017

(65) Prior Publication Data
US 2017/0146403 A1 May 25, 2017

Related U.S. Application Data

(63) Continuation of application No. 14/215,681, filed on Mar. 17, 2014.
(Continued)

(51) Int. Cl.
*G01J 3/28* (2006.01)
*H01L 27/146* (2006.01)
(Continued)

(52) U.S. Cl.
CPC .......... *G01J 3/2823* (2013.01); *A61B 5/0075* (2013.01); *G01J 3/0264* (2013.01); *G01J 3/12* (2013.01);
(Continued)

(58) Field of Classification Search
CPC .......... G01J 3/2823; G01J 3/12; G01J 3/0264; G01N 21/359
See application file for complete search history.

(56) References Cited

U.S. PATENT DOCUMENTS 7,990,533 B2 8/2011 Maier et al.
8,167,794 B2 5/2012 Matsumoto et al.
(Continued)

FOREIGN PATENT DOCUMENTS

WO 2014074569 A1 5/2014

OTHER PUBLICATIONS

Wang et al., Three-Dimensional Imaging of Ureter With Endoscopic Optical Coherence Tomography, Urology (May 2011), 77(5):1254-1258.

*Primary Examiner* — Tony Ko
(74) *Attorney, Agent, or Firm* — Pepper Hamilton LLP (57) ABSTRACT

The present disclosure provides systems and methods for determining the presence of a target material in a sample. In general terms, the system and method disclosed herein provide collecting interacted photons from a sample having a target material. The interacted photons are passed through a tunable filter to a VIS-NIR detector where the VIS-NIR detector generates a VIS-NIR hyperspectral image representative of the filtered interacted photons. The hyperspectral image of the filtered interacted photons is analyzed by comparing the hyperspectral image of the filtered interacted photons to known hyperspectral images to identify the presence of a target material in a sample. The systems and methods disclosed herein provide easy identification of the presence of a target material in a sample.

29 Claims, 5 Drawing Sheets

Related U.S. Application Data (60) Provisional application No. 61/793,962, filed on Mar. 15, 2013.

(51) Int. Cl.
*G01N 21/31* (2006.01)
*G01N 21/359* (2014.01)
*A61B 5/00* (2006.01)
*G01J 3/02* (2006.01)
*G01J 3/12* (2006.01)

(52) U.S. Cl.
CPC ........... *G01N 21/31* (2013.01); *G01N 21/359* (2013.01); *H01L 27/14625* (2013.01); *G01J 2003/1213* (2013.01); *G01J 2003/2826* (2013.01); *G01N 2201/1293* (2013.01)

(56) References Cited

U.S. PATENT DOCUMENTS

| | | | |
|---|---|---|---|
| 8,289,513 B2 * | 10/2012 | Nelson | G01J 3/02 356/326 |
| 2011/0012916 A1 * | 1/2011 | Nelson | G01J 3/02 345/593 |
| 2012/0083678 A1 | 4/2012 | Drauch et al. | |
| 2013/0176568 A1 | 7/2013 | Priore et al. | |
| 2016/0213252 A1 | 7/2016 | Hillman et al. | |

\* cited by examiner

SYSTEM AND METHOD FOR DETECTING TARGET MATERIALS USING A VIS-NIR DETECTOR

CROSS-REFERENCE TO RELATED APPLICATIONS

This application is a continuation application of U.S. patent application Ser. No. 14/215,681 filed Mar. 17, 2014 entitled "System and Method for Detecting Target Materials Using a VIS-NIR Detector," which claims benefit of and priority to U.S. Provisional Application Ser. No. 61/796,962 entitled "Portable VIS-NIR Detector and Method for use thereof" and filed Mar. 15, 2013, the disclosure of each of which is incorporated by reference herein in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of an image gathering optic. For example, a microscope is typically employed for the analysis of sub-micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon (Si) charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems.

Spectroscopic imaging of a sample is commonly implemented by one of two methods. First, point-source illumination can be used on a sample to measure the spectra at each point of the illuminated area. Second, spectra can be collected over the entire area encompassing a sample simultaneously using an electronically tunable optical imaging filter such as an acousto-optic tunable filter (AOTF), a multi-conjugate tunable filter (MCF), or a liquid crystal tunable filter (LCTF). Here, the organic material in such optical filters is actively aligned by applied voltages to produce the desired bandpass and transmission function. The spectra obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR) wavelengths, long wave infrared wavelengths (LWIR), and to some overlapping ranges.

The Applicants hereto have found that use of hyperspectral imaging in the VIS-NIR range of wavelengths provides a useful tool for the identification of target materials in a sample.

SUMMARY

In an embodiment a system for identifying a target material in a sample may include a first collection optic configured to collect a plurality of interacted photons. Interacted photons are those photons that have interacted with the sample. The system further includes a tunable filter configured to filter a first plurality of interacted photons collected from the first collection optic. The tunable filter is configured to filter the first plurality of interacted photons into a plurality of wavelengths to generate filtered interacted photons. In the system, a VIS-NIR detector is configured to detect the filtered interacted photons and to generate a VIS-NIR hyperspectral image representation of the filtered interacted photons. The system further includes a processor configured to analyze the VIS-NIR hyperspectral image of the filtered interacted photons by comparing the VIS-NIR hyperspectral image of the filtered interacted photons to a database of known VIS-NIR hyperspectral images in order to identify the presence of the target material.

In another embodiment, the system may include a second collection optic configured to collect a second plurality of interacted photons. In one embodiment a RGB detector is configured to detect the second plurality of interacted photons and to generate a RGB image representation of the second plurality of interacted photons.

In another embodiment the system may include an illumination source configured to provide photons that interact with a sample to generate interacted photons. In one embodiment, the system described herein may be housed in a portable or handheld device.

In an embodiment disclosed herein, a method for identifying target material in a sample is provided. The method includes collecting a plurality of interacted photons from the plurality of interacted photons have interacted with the sample. The method further provides directing the first plurality of interacted photons through a tunable filter to generate a plurality of filtered photons where the filter separates the photons into a plurality of wavelengths. The method further provides detecting the first plurality of interacted photons with a VIS-NIR hyperspectral detector where the VIS-NIR detector generates a hyperspectral representation of the first plurality of filtered photons. The method further includes analyzing the VIS-NIR hyperspectral image of the filtered interacted photons by comparing the VIS-NIR hyperspectral image of the filtered interacted photons to a database of known hyperspectral images to identify the presence of the target material.

DETAILED DESCRIPTION

Reference will now be made in detail to embodiments of the present disclosure, examples of which are illustrated in the accompanying drawings. Wherever possible, the same reference numbers will be used throughout the specification to refer to the same or like parts.

Figure 1A:
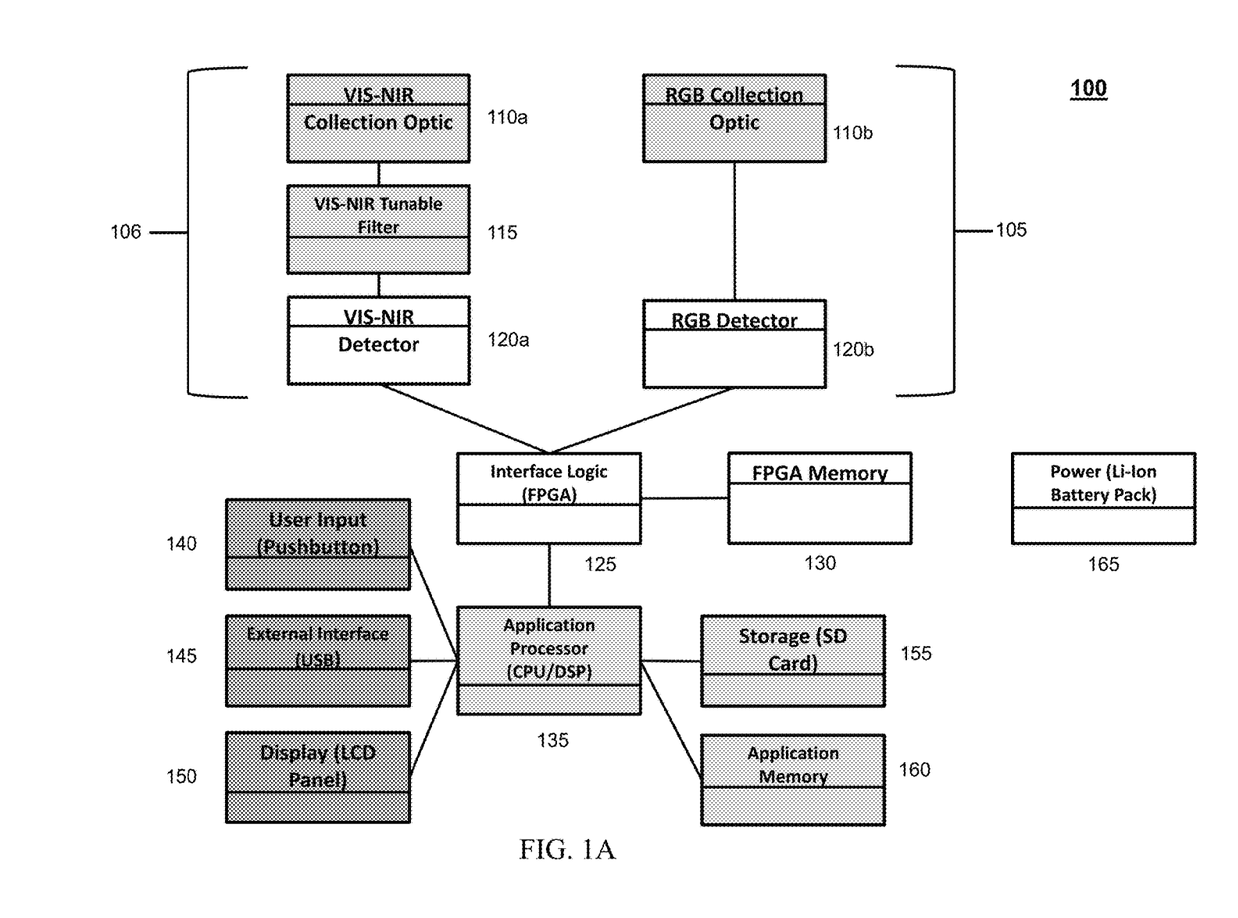
FIG. 1A is a schematic illustration of an illustrative system for identifying a target material according to an embodiment.
Figure 1B:
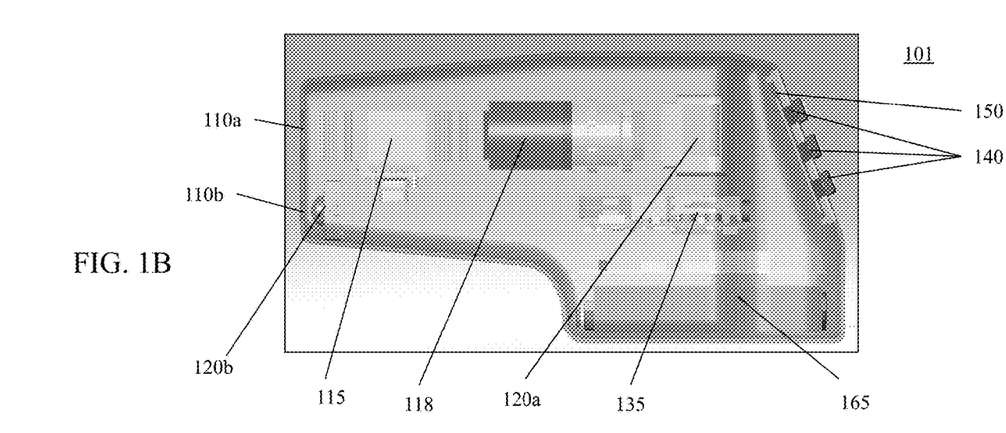
FIG. 1B is a schematic illustration of an illustrative portable system for identifying a target material according to an embodiment.
Figure 1C:
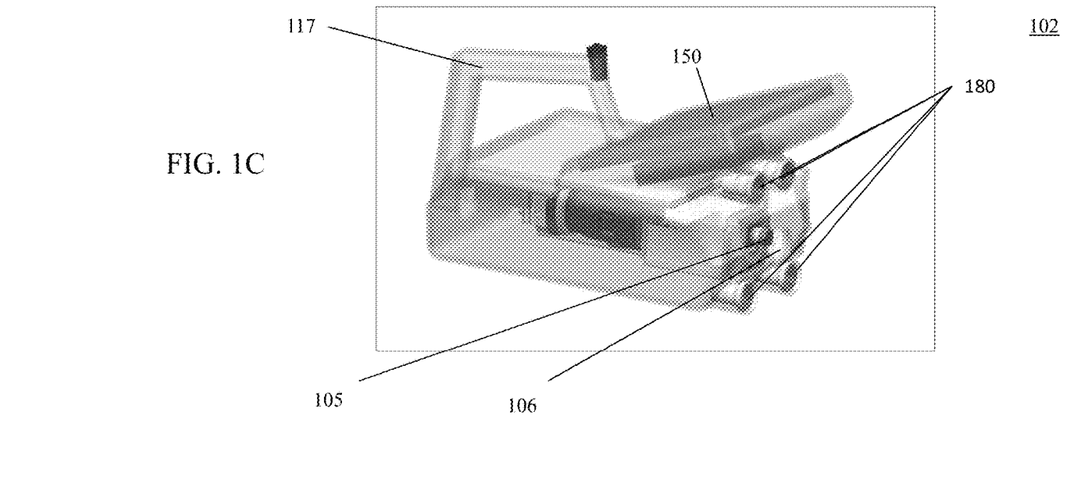
FIG. 1C is a schematic illustration of an illustrative handheld system for identifying a target material according to an embodiment.

FIGS. 1A, 1B, and 1C illustrate exemplary embodiments of a system 100 according to embodiments herein. In one embodiment of the present system, the system 100 is housed in a portable or handheld unit. FIG. 1B and FIG. 1C illustrate an example of a portable and a handheld unit, respectively, featuring the system 100. In another embodiment, the system 100 contemplates designs to accommodate other portable configurations, such as, for example, a design having objectives on movable arms and the like.

Referring now to FIG. 1A, the system 100 comprises a RGB optical subsystem 105. The RGB optical subsystem 105 includes a RGB collection optic 110b and a RGB detector 120b. In one embodiment, the RGB collection optic 110b is a RGB lens. The RGB collection optic 110b is configured to collect a plurality of photons that have interacted with a sample. As used herein, "interacted photons" comprise photons scattered by a sample, photons absorbed by a sample, photons reflected by a sample, photons emitted by a sample or any combination thereof. In one embodiment, the RGB detector 120b is a RGB camera. The RGB collection detector 120b is configured to detect the interacted photons that have been collected from the RGB collection optic 110b. In one embodiment, the RGB optical subsystem 105 generates a RGB image representative of a location on a sample representative of the interacted photons collected from the RGB collection optic 110b.

In another embodiment, the system 100 comprises a VIS-NIR subsystem 106. The VIS-NIR subsystem 106 may include a VIS-NIR collection optic 110a, a VIS-NIR tunable filter 115 and a VIS-NIR detector 120a. The VIS-NIR detector, as used herein, may be configured to detect any wavelength as apparent to those of skill in the art in view of this disclosure. In one embodiment, the VIS-NIR detector is configured to detect wavelengths from about 400 nm to about 1,100 nm. It is understood that the VIS-NIR detector can be configured to detect wavelengths in any subset of wavelengths within those disclosed herein based on a subset of wavelengths that may be of particular interest. In one embodiment, the VIS-NIR collection optic 110a is a VIS-NIR lens. The VIS-NIR collection optic 110a is configured to collect a plurality of photons that have interacted with the sample. The VIS-NIR tunable filter 115 is configured in a sequential manner with the VIS-NIR collection optic 110a to filter photons collected from the VIS-NIR collection optic. In another embodiment, the VIS-NIR detector 120a is sequentially configured with the VIS-NIR tunable filter to detect photons filtered by the VIS-NIR tunable filter 115. The VIS-NIR detector 120a, upon detection of the filtered photons, generates a VIS-NIR hyperspectral image representative of the filtered photons. In one embodiment, the VIS-NIR hyperspectral image contemplated herein is a collection of data images over a range of, for example, from 400 nm to about 1,100 nm. The VIS-NIR hyperspectral imaging provides detailed color information to a user and provides good color discrimination between different materials of interest.

In one embodiment, the system 100 generates the RGB image and the VIS-NIR hyperspectral image simultaneously. That is, the system 100 can operate to generate a RGB image while at the same time the system 100 can generate a VIS-NIR hyperspectral image without the need for consecutively detecting the RGB image and the VIS-NIR hyperspectral image.

The system 100 can be used to determine the presence of the target material in the sample. Applications where the system 100 would be suitable for providing identification of a target include, for example, applications in the areas of anatomic pathology (including dermatological applications), forensic crime scene investigation or reconstruction (blood/body fluid detection and analysis), counterfeit detection (including art work and questioned/security documents), threat detection (chemical, biological, and explosive materials, other hazardous materials, and drugs), and pharmaceuticals including ingredient-specific particle sizing and other applications as would be apparent to those of skill in the art in view of this disclosure. Identification of the presence of a target material in the sample may include detecting, identifying, classifying, or any combination thereof.

In one embodiment of the system, the VIS-NIR tunable filter 115 is configured to filter a plurality of interacted photons into a plurality of wavelength bands. In another embodiment, the VIS-NIR tunable filter 115 may comprise a liquid crystal tunable filter, a multi-conjugate tunable filter, an acousto-optical tunable filters, a Lyot liquid crystal tunable filter, a Evans Split-Element liquid crystal tunable filter, a Solc liquid crystal tunable filter, a Ferroelectric liquid crystal tunable filter, a Fabry Perot liquid crystal tunable filter, or any combination thereof.

In one embodiment of the present system 100, the VIS-NIR detector 120a features a focal plane array. In another embodiment of the present system, the VIS-NIR detector 120a may comprise a detector including, for example, a InGaAs detector, a CMOS detector, an InSb detector, a MCT detector, an ICCD detector, a CCD detector, or any combination thereof.

The system 100 further comprises an field programmable gate array ("FPGA") 125 or interface logic that is in communication with the VIS-NIR detector 120a. In another embodiment, the FPGA 125 is in communication with the RGB detector 120b. The FPGA 125 may further include a FPGA memory source 130. The FPGA 125 may further be in communication with an application processor 135. In one embodiment, the application processor 135 is, for example, a CPU, a digital signal processor, or combinations thereof. The application processor 135 may further be in communication with interface features or peripherals, such as, for example, a user input 150, such as input buttons, an external interface 145, such as a USB, a user display 150, such as a LCD panel display, storage memory 155, such as an SD card, application memory 160, and other peripherals as would be apparent to those of skill in the art in view of this disclosure. In one embodiment of the system 100, the FPGA 125, application processor 135, memory source 130, storage memory 155, and application memory 160 are configured to operate the system 100 to analyze and store collected data and store reference data. In one embodiment, the system 100 comprises a reference database having a plurality of reference data sets where each reference data set is associated with a known material. Each reference data set may comprise a hyperspectral image of a known material such that the hyperspectral image obtained from the sample via the system 100 can be compared to each reference data set to identify the sample and the target material to determine the presence of the target material in the sample. It is understood that the target material is of known composition and the system 100 provides the capability of determining the presence of the target material in the sample by comparing hyperspectral images obtained from the sample and the target material to known hyperspectral images to identify the presence of the target material. The system 100 distinguishes the hyperspectral image of the sample from the hyperspectral image of the target material, if present. Once the identification of the sample and the target material are obtained by the system 100, the result of the identification can be reported to a user through the display 150. The system 100 may also comprise a battery pack 145 for supplying power to the system 100.

The system 100 can be configured to operate at various distances from the VIS-NIR collection optic 110a and the RGB collection optic 110b to the sample. The operating distance is dependent on the specifications of the VIS-NIR collection optic 110a and the RGB collection optic 110b and can be about 0.5 m or greater. In one embodiment, the operating range of the system 100 is about 0.5 m or greater. In another embodiment, the operating range of the system 100 is about 5 m or greater. In yet another embodiment, the operating range of the system 100 is from about 1 m to about 20 m. In another embodiment, the operating range of the system 100 is from about 0.5 m to about 10 m. It is apparent to one of skill in the art that the operating range of the system can be configured to operate in any range within those recited. Further, in one embodiment, the system 100 is capable of operating with adjustable optics such that the operating range of the system 100 can be adjusted without the need to modify the VIS-NIR collection optic 110a and the RGB collection optic 110b. In another embodiment, the collection optics may be configured to change the Field of View ("FOV") with regard to the sample. Configuring the FOV can be accomplished by, in a fixed collection optics system, by changing the collection optics to achieve the desired FOV or, in an adjustable collection optic system, by adjusting the collection optics to achieved the desired FOV. The desired FOV would be apparent to those of skill in the art in view of this disclosure. The system 100 can further include other optical devices such as, for example, additional lens, other image gathering optics, arrays, mirrors, beam splitters and the like. Additional elements suitable for use with the system 100 are apparent to those of skill in the art in view of this disclosure.

The system 100 can further be configured to generate hyperspectral images of a sample having a target material in near real time. In one embodiment, the system 100 tracks a sample generating up to 2 frames/second to allow for near real time analysis of a sample.

In one embodiment, the system 100 includes an illumination source. The illumination source can be one illumination source or a plurality of illumination sources. The illumination source can be ambient light or light provided to the sample from an active source working in conjunction with the system 100. In one embodiment, the illumination source illuminates the sample from a variety of different angles. An active illumination source when used with the system 100 enables the system to operate in low or variable light conditions. Any illumination sources suitable for use with the system 100 can be used and such illumination sources would be apparent to those of skill in the art in view of this disclosure.

FIG. 1B illustrates an illustrative portable system 101 for identifying a target material in a sample according to an embodiment. The portable system 101 features a VIS-NIR lens 110a and a RGB lens 110b in close proximity to allow for the collection of photons from a sample for analyzing a RGB image and a VIS-NIR hyperspectral image in one step. The VIS-NIR lens 110a collects photons from a sample and directs the photons through a VIS-NIR liquid crystal tunable filter ("LCTF") 115. The photons from the VIS-NIR LCTF 115 then pass through a focusing lens 118 which focus the photons before passing the photons on to the VIS-NIR camera 120a. The VIS-NIR camera 120a detects the photons passing from the focusing lens 118 and generates a VIS-NIR hyperspectral image representative of the photons. A processor 135 in communication with the VIS-NIR camera 120a analyzes the hyperspectral image to determine the presence of the target material in a sample. The portable system 101 further includes a RGB lens 110b and a RGB camera 120b where the RGB camera is configured to detect photons collected from the RGB lens 110b. The RGB camera 120b generates a RGB image representative of the photons collected from the RGB lens 110b. The RGB camera 120b is further in communication with the processor 135 for analyzing the RGB image. The portable system includes user interface controls 140 to permit the user to interact with the portable system 101. Further, the portable system 101 includes a display 150 for displaying information obtained by the portable system to a user. The portable system 101 further includes a power source 165 for operating the portable system remotely.

FIG. 1C depicts an illustrative handheld system 102 to permit a user to carry the system for identifying a target material according to an embodiment. The handheld system 102 includes a handle 117 for being carried by a user. The handheld system 102 further includes active illumination sources 180 for illuminating a sample to generate photons that interact with a sample. The active illumination sources 180 enable the handheld system 102 to operate in remote locations having inadequate illumination. The handheld system 102 includes a VIS-NIR collection lens aperture 106 and a RGB collection lens aperture 105 for collecting photons generated by a sample. The handheld system 102 further includes a display 150 for conveying data obtained by the handheld system 102 to a user. In operation, the handheld system 102 operates in similar fashion to the system 100, as described herein.

Figure 2:
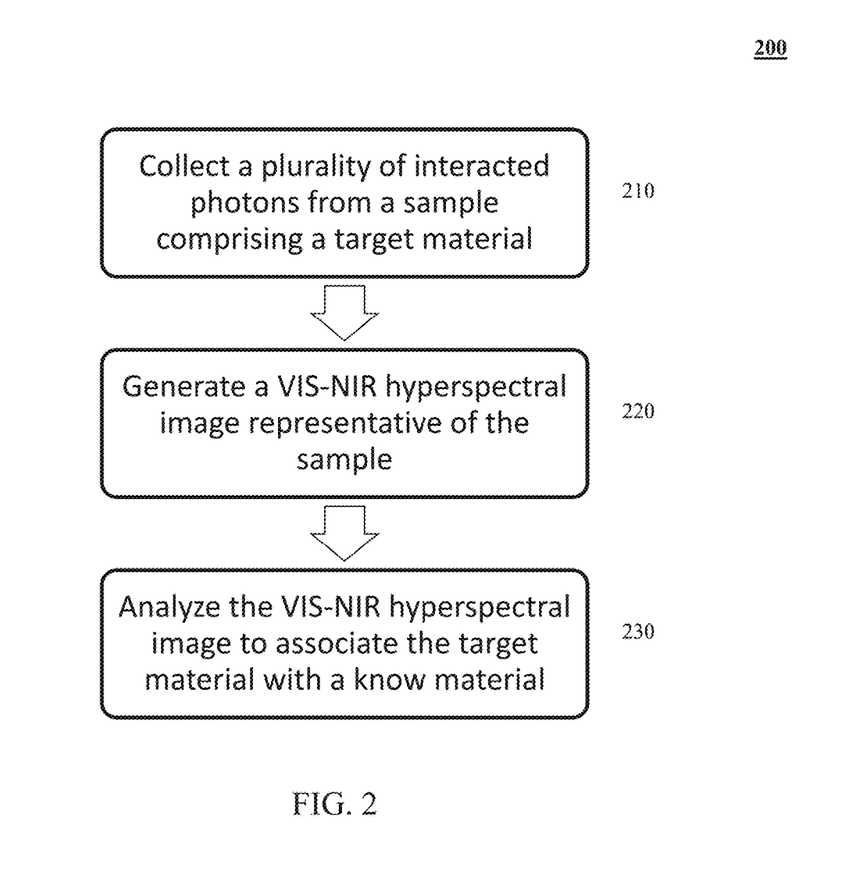
FIG. 2 is a flow-chart illustrating an illustrative method for identifying a target material according to an embodiment.

FIG. 2 depicts a flow diagram of an illustrative method 200 for analyzing a sample comprising a target material according to an embodiment. The method 200 may comprise collecting 210 a plurality of interacted photons from the sample comprising a target material in step 210. These interacted photons may be generated by illuminating the sample using an active illumination, a passive illumination, or any combination thereof. The interacted photons may comprise photons scattered by the sample, photons reflected by the sample, photons absorbed by the sample, photons emitted by the sample, or any combination thereof.

In one embodiment of the method 200, the interacted photons may be passed through a tunable filter. The tunable filter is configured to filter the interacted photons into a plurality of wavelength bands. A VIS-NIR hyperspectral image may be generated 220 representative of the sample comprising a target material. The VIS-NIR hyperspectral image may be analyzed 230. In one embodiment, the VIS-NIR hyperspectral image is analyzed 230 by comparing the hyperspectral image of the sample and the hyperspectral image of the target material to a reference data set where the reference data set includes known hyperspectral images to identify the presence of the target material in the sample. In one embodiment, the comparison is accomplished by applying one or more chemometric techniques. Chemometric techniques suitable for use in the method include: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, and Bayesian fusion. It is also contemplated that more than one chemometric technique may be applied. It is further contemplated that any chemometric method as known to those of skill in the art may be applied. In one embodiment, the analysis may detect a target material, associate the target material with a known material, detect a difference between the target and the sample, detect more than one target in the sample, or any combination thereof.

EXAMPLES

Example 1

Figure 3:
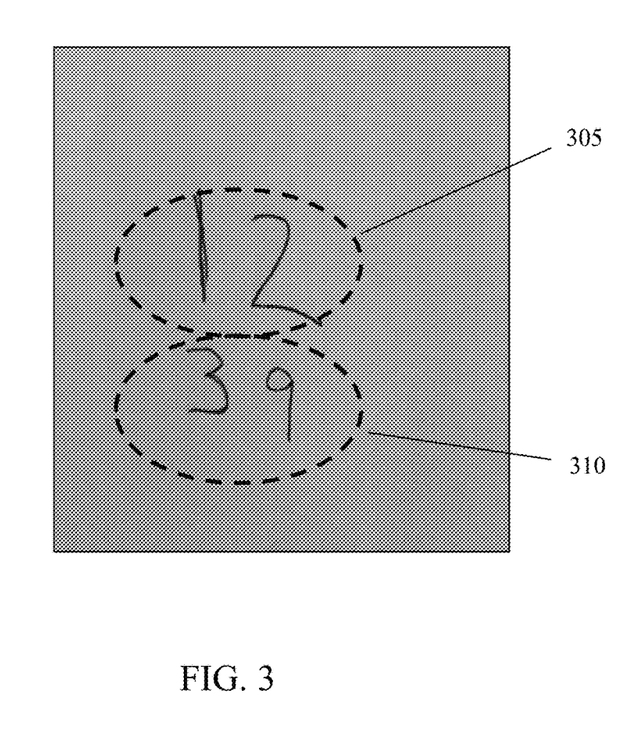
FIG. 3 illustrates a sample material having two ink compositions where one ink is a target material according to an embodiment.
Figure 4:
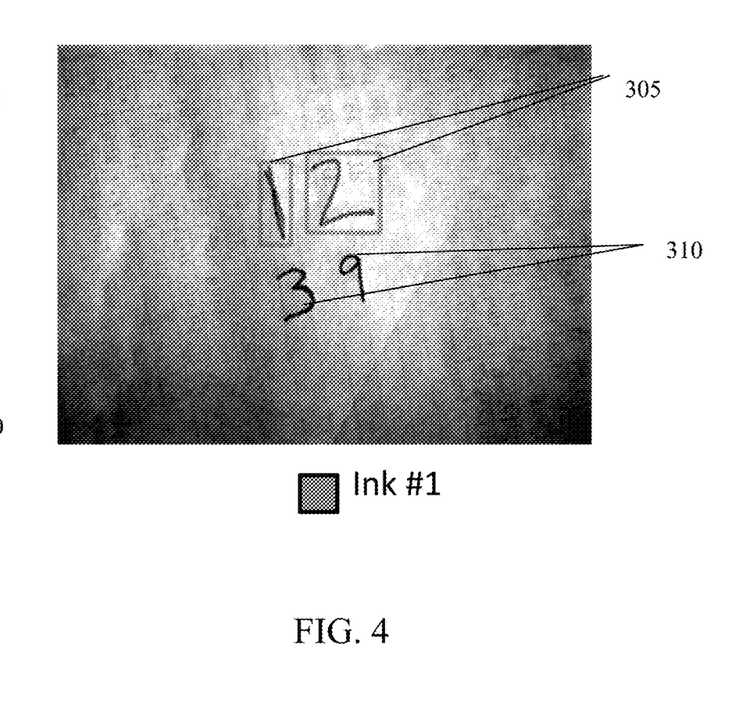
FIG. 4 illustrates a VIS-NIR hyperspectral image of a sample identifying a target ink in the sample according to an embodiment.

FIG. 3 and FIG. 4 illustrate an example using the disclosed system for identifying a target material in a sample. In this example, the VIS-NIR detector was configured to identify the presence of one ink having a different composition from a second ink. In FIG. 3, a sample is illustrated where the sample includes a first black ink 305, represented by the drawn number "12," and the second black ink 310, represented by the drawn number "39." Both inks were drawn on paper. Separate VIS-NIR hyperspectral spectra were obtained for each of the two different sets of black ink 305, 310. A subset of wavelengths was selected in order to identify the presence of the first black ink 305 in the sample. FIG. 4 shows the VIS-NIR detection image of the sample containing both the first black ink 305 and the second black ink 310. Once the VIS-NIR spectra was obtained for the sample, the VIS-NIR image was compared the known VIS-NIR spectra for the different inks. After the comparison, the presence of the first black ink 305 was identified in the field of view. The first black ink 305 is shown with a green hue and is highlighted in the green boxes. In this Example, a VIS-NIR detector was used to produce near real-time detections of the presence of the first black ink 305 in the field of view.

Example 2

Figure 5:
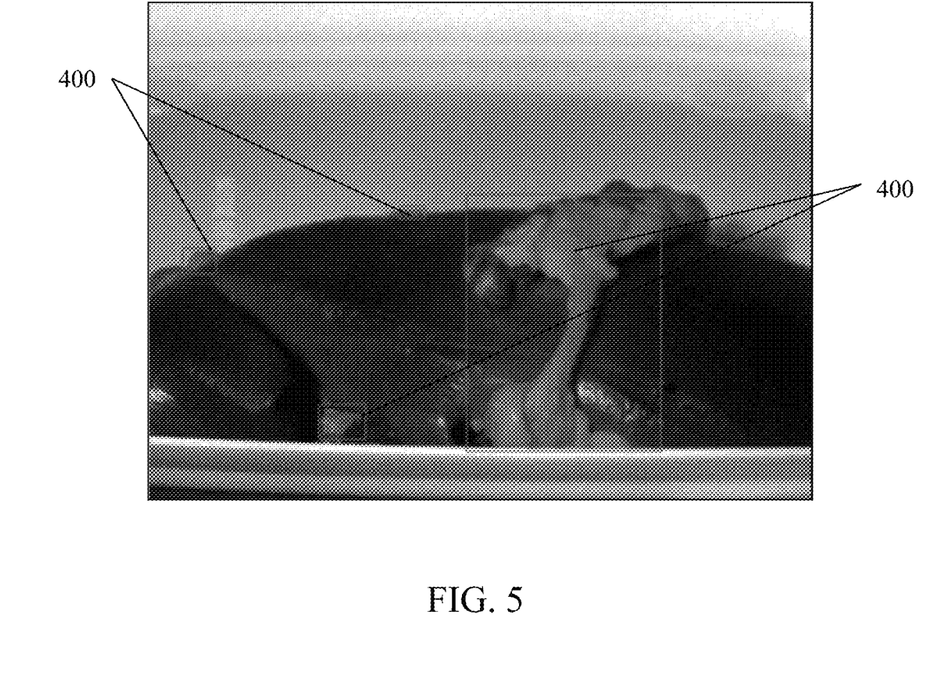
FIG. 5 illustrates a VIS-NIR hyperspectral image of a kidney sample identifying blood vessels and fat tissue in the kidney sample according to an embodiment.

FIG. 5 illustrates another example using the disclosed system for identifying a target material in a sample. In this example, a VIS-NIR detector is configured to identify blood vessels and fat tissue from other tissue parts of a kidney. Separate VIS-NIR spectra was obtained for kidney sample tissues as well as for blood vessels and fat tissue. A subset of wavelengths was selected to identify the presence of blood vessels and fat tissue. The kidney sample was analyzed by a VIS-NIR detector producing the result shown in FIG. 5. The VIS-NIR spectra of the kidney sample was compared to known VIS-NIR spectra of a kidney sample, blood vessels, and fat tissue. After the comparison, blood vessels and fat tissue 400 were observed in the sample. The blood vessels and fat tissue 400 show up in the VIS-NIR image having a green hue. In this Example, a VIS-NIR detector was used to produce near real-time detections of the blood vessels and fat tissue within the field of view.

While the disclosure has been described in detail in reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A system for identifying a target material in a sample, the system comprising:
    a first collection optic configured to collect a plurality of interacted photons that have interacted with the sample;
    a tunable filter configured to filter a first plurality of interacted photons collected from the first collection optic into a plurality of wavelengths to generate filtered interacted photons;
    a VIS-NIR detector configured to detect the filtered interacted photons, wherein the VIS-NIR detector generates a VIS-NIR hyperspectral image representation of the filtered interacted photons; and
    a processor configured to analyze the VIS-NIR hyperspectral image of the filtered interacted photons by comparing the VIS-NIR hyperspectral image of the filtered interacted photons to a database of known VIS-NIR hyperspectral images in order to identify the presence of the target material,
    wherein the system is housed in a portable or handheld unit.

2. The system of claim 1, further comprising:
    a second collection optic configured to collect a second plurality of interacted photons; and
    a RGB detector configured to detect the second plurality of interacted photons collected from the second collection optic, wherein the RGB detector is configured to generate a RGB image representation of the second plurality of interacted photons.

3. The system of claim 2, wherein the VIS-NIR hyperspectral image and the RGB image are generated substantially simultaneously.

4. The system of claim 1, further comprising an illumination source, wherein the illumination source is configured to provide photons that interact with the sample to generate the plurality of interacted photons.

5. The system of claim 1, wherein the tunable filter comprises a liquid crystal tunable filter, a multi-conjugate tunable filter, an acousto-optical tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, or any combination thereof.

6. The system of claim 1, wherein the VIS-NIR detector comprises an InGaAs detector, a CMOS detector, an InSb detector, a MCT detector, an ICCD detector, a CCD detector, or any combination thereof.

7. The system of claim 1, wherein the VIS-NIR detector comprises a focal plane array.

8. The system of claim 1, further comprising a display configured to display analysis information obtained by the system to a user.

9. The system of claim 1, further comprising a user interface configured to receive one or more inputs from a user to interact with the system.

10. The system of claim 1, wherein the processor is further configured to analyze the VIS-NIR hyperspectral image generated from the filtered interacted photons by applying a chemometric technique.

11. The system of claim 10, wherein the chemometric technique comprises principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion or any combination thereof.

12. The system of claim 1, further comprising a power source for operating the system remotely.

13. A method for identifying a target material in a sample, the method comprising:
collecting a plurality of interacted photons from the sample, wherein the plurality of interacted photons have interacted with the sample;
directing a first plurality of interacted photons through a filter to generate a first plurality of filtered photons, wherein the filter separates the first plurality of interacted photons into a plurality of wavelengths;
detecting the first plurality of filtered photons with a VIS-NIR hyperspectral image detector,
generating a VIS-NIR hyperspectral image of the first plurality of filtered photons; and
analyzing the VIS-NIR hyperspectral image of the filtered interacted photons by comparing the VIS-NIR hyperspectral image of the filtered interacted photons to a database of known hyperspectral images to identify the presence of the target material,
wherein the method is performed in a portable or handheld unit.

14. The method of claim 13, further comprising:
collecting a second plurality of interacted photons;
detecting the second plurality of interacted photons with a RGB detector, and
generating a RGB image representation of the second plurality of interacted photons.

15. The method of claim 14, wherein the VIS-NIR hyperspectral image of the filtered interacted photons and the RGB image are generated simultaneously.

16. The method of claim 14, further comprising illuminating the sample with an illumination source, wherein the illumination source provides photons that interact with the sample to generate the second plurality of interacted photons.

17. The method of claim 13, further comprising illuminating the sample with an illumination source wherein, the illumination source provides photons that interact with the sample to generate the first plurality of interacted photons.

18. The method of claim 13, wherein analyzing the VIS-NIR hyperspectral image further comprises applying a chemometric technique.

19. The method of claim 13, wherein the portable or handheld unit includes a power source for operating the portable or handheld unit remotely.

20. A system for identifying a target material in a sample, the system comprising:

an illumination source configured to provide photons that interact with the sample to generate a plurality of interacted photons;
a first collection optic configured to collect a first plurality of interacted photons, wherein the first plurality of interacted photons includes photons that have interacted with the sample;
a second collection optic configured to collect a second plurality of interacted photons where the second plurality of interacted photons includes photons that have interacted with the sample;
a tunable filter configured to filter the first plurality of interacted photons collected from the first collection optic into a plurality of wavelengths to generate filtered interacted photons;
a VIS-NIR detector configured to detect the filtered interacted photons, wherein the VIS-NIR detector generates a VIS-NIR hyperspectral image of the filtered interacted photons;
a RGB detector configured to detect the second plurality of interacted photons, wherein the RGB detector generates a RGB image representation of the second plurality of interacted photons; and
a processor configured to analyze the VIS-NIR hyperspectral of the filtered interacted photons and compare the VIS-NIR hyperspectral image of the filtered interacted photons to a database of known VIS-NIR hyperspectral images in order to identify the target material,
wherein the system is housed in a portable or handheld unit.

21. The system of claim 20 wherein the VIS-NIR hyperspectral image and the RGB image are generated simultaneously.

22. The system of claim 20, wherein the tunable filter comprises a liquid crystal tunable filter, a multi-conjugate tunable filter, an acousto-optical tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, or any combination thereof.

23. The system of claim 20, wherein the VIS-NIR detector comprises a InGaAs detector, a CMOS detector, an InSb detector, a MCT detector, an ICCD detector, a CCD detector, or any combination thereof.

24. The system of claim 20, wherein the VIS-NIR detector comprises a focal plane array.

25. The system of claim 20, further comprising a display configured to display VIS-NIR hyperspectral analysis information, RGB image information, or any combination thereof obtained by the system to a user.

26. The system of claim 20, further comprising a user interface configured to receive one or more inputs from a user to interact with the system.

27. The system of claim 20, wherein the processor is further configured to analyze the VIS-NIR hyperspectral image of the filtered interacted photons by applying a chemometric technique.

28. The system of claim 27, wherein the chemometric technique comprises: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion or any combination thereof.

29. The system of claim 20, further comprising a power source for operating the system remotely.

\* \* \* \* \*